United States Patent [19]

Koopmann et al.

[11] 4,238,952

[45] Dec. 16, 1980

[54] METHOD OF DETERMINING CHARACTERISTIC RHEOLOGICAL QUANTITIES OF VISCOELASTIC MATERIALS

[75] Inventors: Rüdiger Koopmann, Langenfeld; Richard Juffa, Cologne, both of Fed. Rep. of Germany

[73] Assignee: Bayer Aktiengesellschaft, Leverkusen, Fed. Rep. of Germany

[21] Appl. No.: 47,977

[22] Filed: Jun. 13, 1979

[30] Foreign Application Priority Data

Jun. 23, 1978 [DE] Fed. Rep. of Germany ....... 2827593

[51] Int. Cl.$^3$ ............................................. G01N 25/02
[52] U.S. Cl. ....................................... 73/15.6; 73/818
[58] Field of Search ................ 73/15.6, 823, 825, 819, 73/818, 821

[56] References Cited

U.S. PATENT DOCUMENTS

| 3,818,751 | 6/1974 | Karper et al. | 73/15.6 |
| 4,074,569 | 2/1978 | Sambrook | 73/15.6 |
| 4,095,461 | 6/1978 | Starita | 73/15.6 |

*Primary Examiner*—Donald O. Woodiel
*Attorney, Agent, or Firm*—Sprung, Felfe, Horn, Lynch & Kramer

[57] ABSTRACT

The invention relates to the determination of characteristic rheological quantities of viscoelastic materials by measuring specific parameters which permit assertions to be made on the properties of the material owing to their functional correlation with the deformation or relaxation.

3 Claims, 4 Drawing Figures

METHOD OF DETERMINING CHARACTERISTIC RHEOLOGICAL QUANTITIES OF VISCOELASTIC MATERIALS

BACKGROUND OF THE INVENTION

The invention relates to a method of determining characteristic rheological quantities of viscoelastic materials, in particular of rubber and rubber mixtures.

More and more, manufacturers are having to observe increasing standards in terms of quality. In addition, early predictions about processing behaviour are useful for the manufacture of products. The development of new products is simplified by characterisation by rheological characteristic quantities. Methods of examination have therefore been under development for a long time but they only meet these requirements to a limited extent.

The parallel plate compression plastimeter is a known method for determining plasticity according to Baader, which was known under the former DIN 53 514 standard.

In this method, a cylindrical body ($\phi$ 10 mm, h=10 mm) is drilled from a so-called skin and subjected to a load on its face after storage at a temperature of 80° C. The force (deformation hardness) which compresses a virgin sample to a height of 4 mm in 30 seconds is sought by repeated testing as a measured value of the viscous behaviour of the material. The expansion of the material, which is designated as deformation elasticity and which can be considered as a measured value of the elastic behaviour of the material, is measured 30 seconds after unloading.

The investigation supplies only two measured values which are not sufficient to characterise the material, since, on the one hand, the stress conditions vary greatly in practice and, on the other hand, the properties of the material can change during processing and statements cannot be made on either point by this examination. Moreover, the search for the corresponding force is time consuming and costly in material, irrespective of the risk of error.

A mooney rotating plastometer in which a corrugated disc rotates in a cylindrical chamber filled with material to be tested, is also used. The viscosity counteracting the rotation of the disc produces a torque, which can be taken as a measure of viscosity. A characteristic quantity can then be determined for the elasticity by means of the back-twist angle of the rotor on uncoupling the drive.

Considerable variations occur in the measurements, particularly as a result of non-stationary, non-homogeneous temperature fields in the sample and varying adhesion to the walls. In particular, they cannot be reproduced sufficiently from laboratory to laboratory.

A mechanical spectrometer is also known, with which the sample is subjected to shearing deformations. The reactions of the sample are then conveyed to a measuring unit by a transformer which measures the forces in directions which are perpendicular to each other. The device is suitable only for research institutes, owing to its complicated structure.

The two last-mentioned measuring devices have the disadvantage that the determination of the dependence of the viscoelastic characteristic quantities on the deformation rate is very time consuming and costly in material, and also materials having the same flow and temperature pre-history have to be used in each case in order to eliminate additional influences.

SUMMARY OF THE INVENTION

The object of the invention is to provide a method of measuring flowable viscoelastic materials which, for a small outlay in the measuring device, material used and time, produces sufficient rheological characteristic quantities such as viscosity, elasticity and their dependence on the deformation rate for reliably determining their quality and processing properties, in which the occurrence of damage to the material must be detectable.

According to the present invention there is provided a method of determining characteristic rheological quantities of viscoelastic materials, in particular rubber and rubber mixtures, in which a cylindrical sample which has been preheated to a specific temperature is compressed by a force on its faces to a predetermined sample height in order to measure the viscosity and in order to give a measurement for the elasticity as a result of the relaxation height after unloading over the same period, characterised in that at least two uniform samples of the same batch are loaded and unloaded with arbitrary forces which differ from each other and which lead to testing periods of between 5 and 150 seconds, whereby during the loading and unloading in each case a period is measured over a section of the path of deformation of the sample at less than 60% of the original height.

It was surprising to the technical expert that viscoelastic materials with their quite specific deformation behaviour, such as the deviation from Newton's flow behaviour, the existence of partial elastic deformation during flowing operations and the presence of relaxation time spectra, produce a change in the height of the sample with time when the force is varied under predetermined test conditions, which change can be represented completely by a function h ($\alpha$ t), the force only entering with the constant $\alpha$.

The measured quantities of force and time which are easy to determine produce, by conversion, values which are proportional to the apparent viscosity and the average deformation rate. All the values required for characterizing the viscosity as a function of the deformation rate in the validity range of the exponential law can be obtained by measuring with two different forces.

It was also surprisingly found that approximately equal relaxation values are obtained independently of the force by selecting the unloaded time equal to the loaded time. The relaxation rate is therefore in a specific relation to the respective deformation rate. The relaxation with its dependence on the deformation rate is therefore also known.

The small requirement in sample material and time for determining the rheological properties of viscoelastic materials permits processing conditions to be determined in advance and makes it easier to monitor the quality. The method is also very advantageous for the development of new products, because practical results can be obtained with few measurements. In addition, the tests demonstrate good selectivity with only slight variations in the test values and high accuracy of testing.

In a particular embodiment of the method, the sample is loaded alternately by equal forces until the predetermined lower height for the sample is reached, so that, without external loading, the sample subsequently returns to an upper height which is determined by the first unloading in a time corresponding to the first deformation period, the respective times being measured over the path section occurring during the respective deformations.

These alternating stresses simulate conditions in processing. After only a few cycles characteristic rheological quantities are obtained which are of practical importance.

In another embodiment of the method, the force on virgin samples is increased step-wise in each case until the material is broken down.

Flowable viscoelastic materials cannot be processed if deformation-induced structures and/or melt-breaking phenomena occur. This limit value can quickly be determined by the above-mentioned tests without a high outlay.

The invention will be further described with reference to the accompanying drawings, in which:

DETAILED DESCRIPTION OF THE INVENTION

Figure 1:
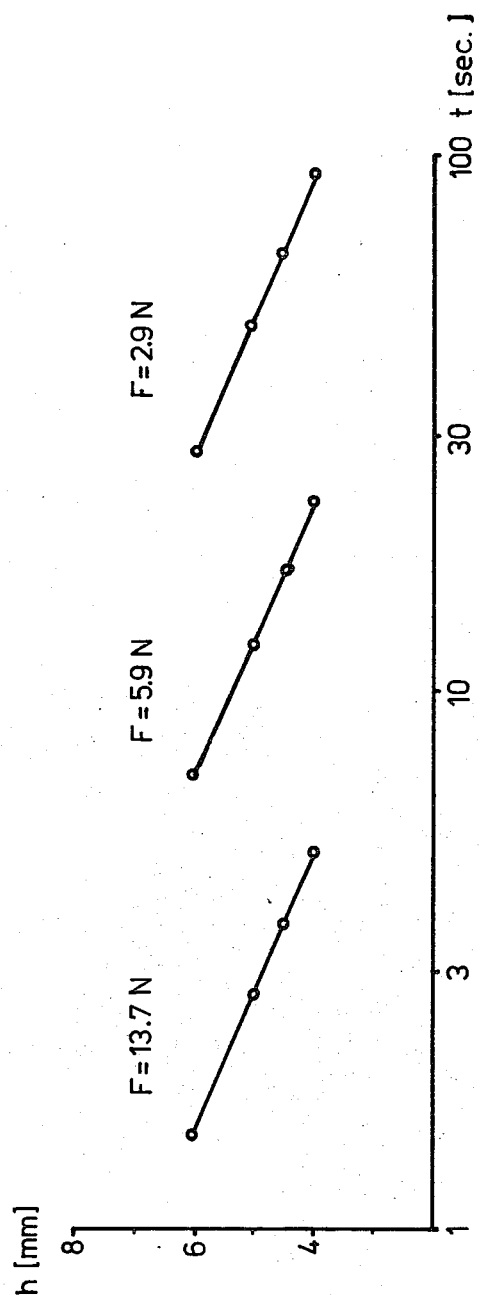
FIG. 1 shows the change in the height of a sample with time under various forces F.

FIG. 1 shows the change in height h (t) of a sample of a viscoelastic material with time when loaded by various constant forces F. It has been found that the curves (straight lines) are functionally equal for all forces.

$$h(t)/h_0 = f(\alpha \cdot t) \quad (1)$$

in which $h_0$ represents the initial height of the sample and $\alpha$ represents a value which is only dependent on F.

The change in height with time can therefore be evaluated in the range of from below 60% of the initial height to an arbitrary height. If, for example, a period $(\Delta t_v)_1$ elapses for a deformation of from 4.5 to 4 mm in height—see FIG. 2—the average deformation rate $\dot{\gamma}$ is proporational to $1/(\Delta t_v)_1$. There is also proportionality between F and the shear force $\tau$. The apparent viscosity $\eta s = \tau/\dot{\gamma}$ is proportional to $(F \cdot (\Delta t_v)_1)$, so this product can be considered as a coefficient of viscosity V. The known exponential law for the dependence of the apparent viscosity $\eta_s$ on the deformation rate $\dot{\gamma}$ thus gives:

$$V = (F\Delta t_v)_1 = K \cdot \left[ \frac{1}{(\Delta t_v)_1} \right]^n \quad (2)$$

wherein K contains all proportionality constants, n represents the viscosity exponent and F and $(\Delta t_v)_1$ are the measured quantities.

Examination of the viscosity of an acrylonitrile butadiene rubber (NBR) produces:

| Testing Period $(t_v)_1$[s] | Comparison Force F[N] | Deformation Time Constant $(\Delta t_v)_1$[s] | Coefficient of Viscosity $V = F \cdot (\Delta t_v)_1$ [Ns] | Coefficient of deformation rate $1/(\Delta t_v)_1[s^{-1}]$ |
|---|---|---|---|---|
| 136.2 | 3.43 | 44.7 | 153.3 | 0.0224 |
| 23.5 | 8.09 | 7.2 | 58.3 | 0.138 |
| 5.0 | 17.66 | 1.5 | 26.5 | 0.667 |

Figure 3:
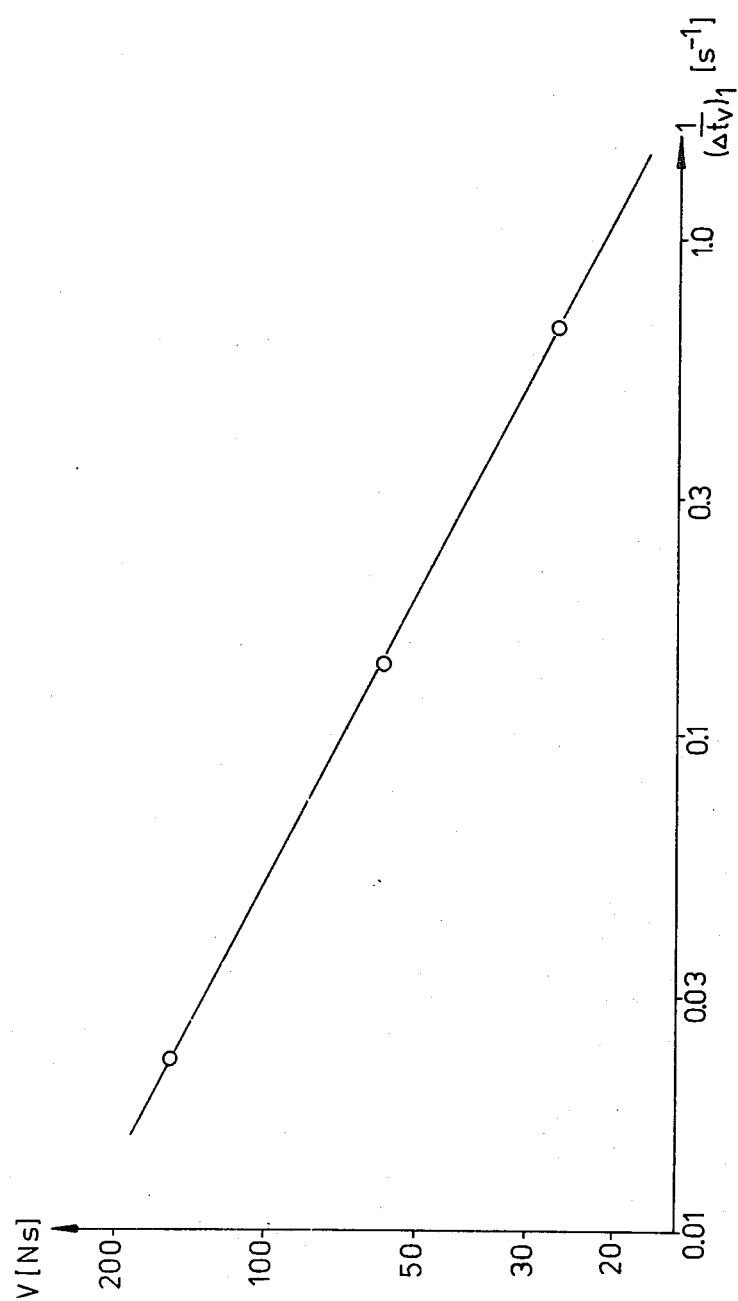
FIG. 3 shows the coefficient of viscosity V as a function of the coefficient of the deformation rate $1/\Delta t_v$.

The plotting of log V against log $(1/\Delta t_v)_1$ in FIG. 3 produces a straight line which is completely characterised by two values. Exponent $n = -0.52$ and the coefficient of viscosity $V_{10} = 70$ [Ns] corresponding to $(\Delta t_v)_1 = 10$ s are selected as characteristic quantities in this case.

The elastic behaviour of the material can be indicated by the percentage relaxation of the height of the sample based on the compression of the sample after the release time $(t_R)_1$ which is equal to the testing time $(t_v)_1$.

Figure 2:
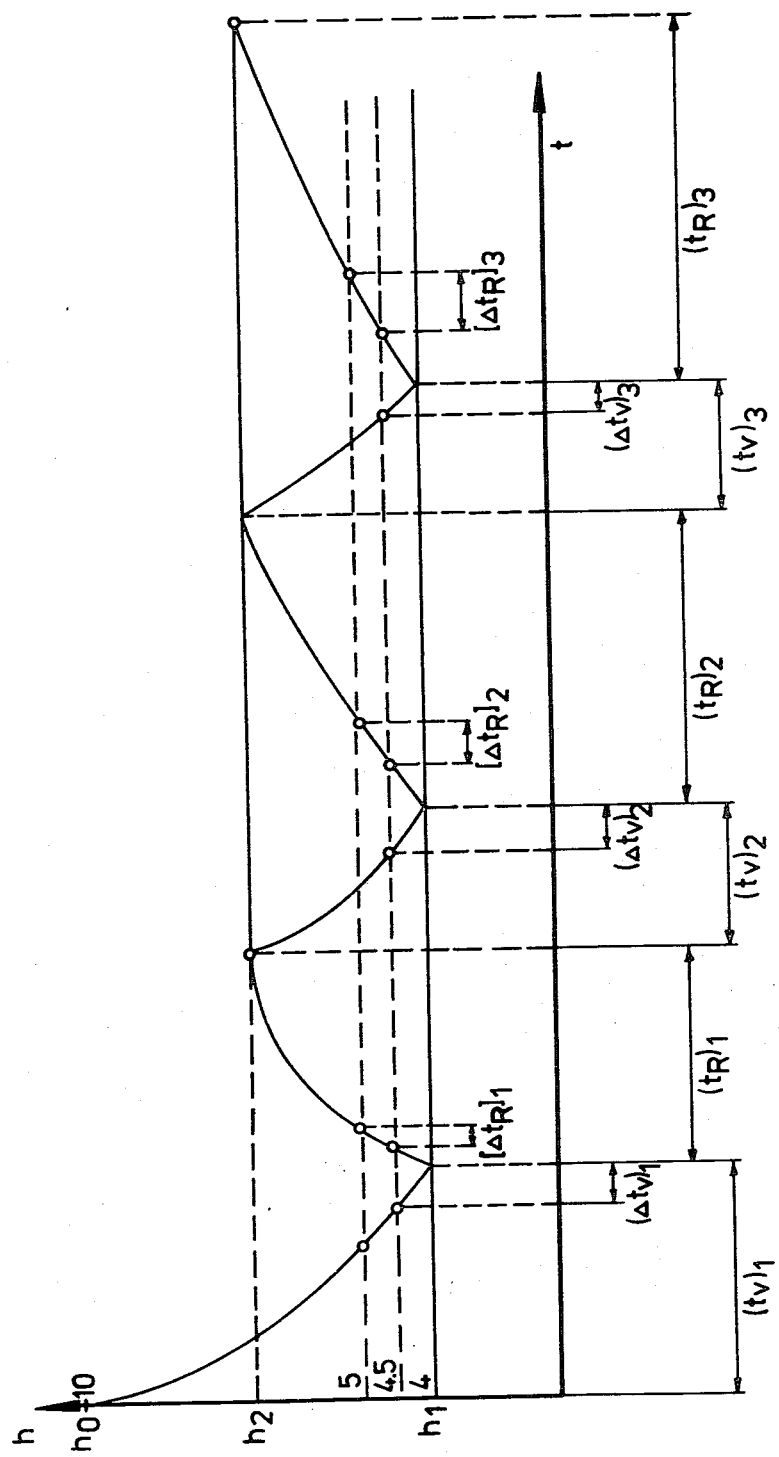
FIG. 2 shows the change in the height with time of loading by a force and relaxation (without force) between two sample heights.

The following calculation is made from the height $h_2$ of the sample, as shown in FIG. 2;

$$R = \frac{h_2 - h_1}{h_0 - h_1} \cdot 100 \quad (3)$$

Examination of the elasticity of an acrylonitrile butadiene rubber (NBR) produces:

| Testing Time $(t_v)$[s] | Deformation Time Constant $(\Delta t_v)_1$[s] | Deformation Rate $1/(\Delta t_v)_1[s^{-1}]$ | Relaxation Height $h_2$[mm] | Relaxation R[%] |
|---|---|---|---|---|
| 136.2 | 44.7 | 0.0224 | 5.58 | 26.3 |
| 23.5 | 7.2 | 0.139 | 5.70 | 28.3 |
| 5.0 | 1.5 | 0.667 | 5.80 | 30.0 |

Figure 4:
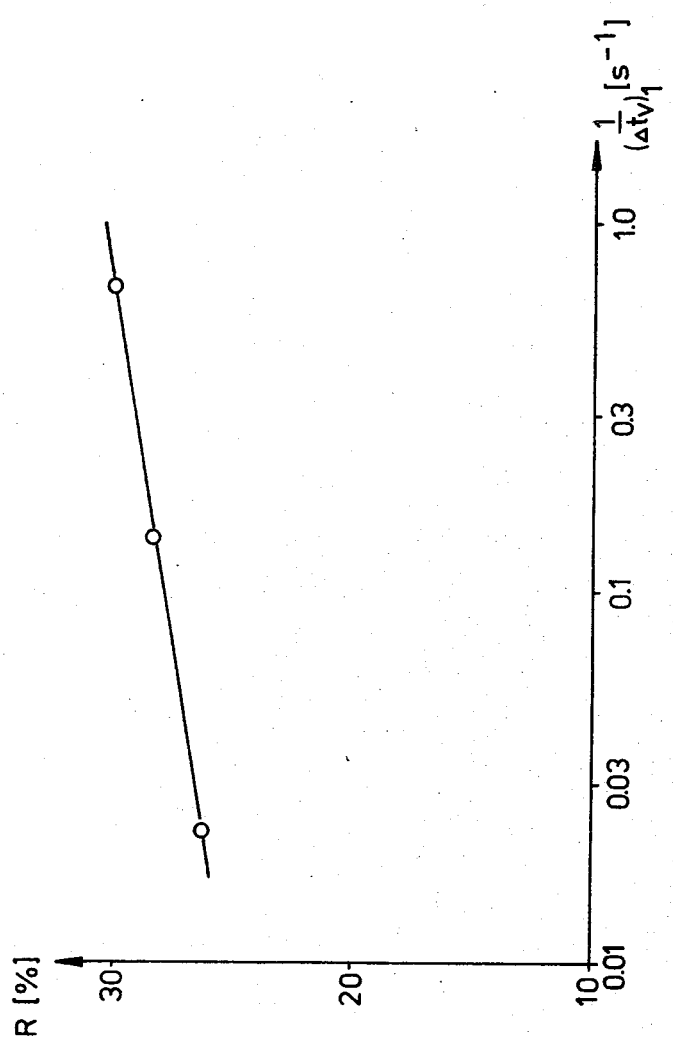
FIG. 4 shows the relaxation R as a function of the coefficient of the deformation rate $1/\Delta t_v$.

The slight dependence on the deformation rate is shown in FIG. 4 by plotting R against log $(1/(\Delta t_v)_1)$ to form a straight line. This is completely characterised by two values such as, for example, by the inclination $m = \Delta R/\Delta \log (\Delta t_v)_1 = 2.5\%$/decade and $R_{10} = 28.0\%$ as the relaxation corresponding to $(\Delta t_v)_1 = 10$ seconds testing time.

The deformation/relaxation procedures can be repeated several times, for example even in direct succession, on the same specimen as in FIG. 2.

With regard to the viscous behaviour of the material, the sample is reloaded after a relaxation to a specific height $h_2$ of the sample in each case with the same force as in the first loading, so that the values n and $V_{10}$ can be determined in the manner described above.

In order to characterise the change in the material with respect to the elastic relaxation, the sample is unloaded repeatedly after reaching the height $h_1$ of the sample in each case and the time $(t_R)_i$ is measured for a predetermined relaxation. Thus, for example, the change in the average relaxation rate can be characterised by the change in the reciprocal time constant $1/(\Delta t_R)_i$.

What we claim is:

1. A method of determining characteristic rheological quantities of viscoelastic materials, comprising the steps of:
   preheating at least two uniform cylindrical samples of the same batch to a specific temperature;
   compressively loading each sample with a force on its opposite faces so as to compress the sample to a predetermined height, each force differing from the other and resulting in a testing period of between 5 and 150 seconds;

unloading the sample; and during loading and unloading in each case, measuring the period over a section of the deformation path in which the sample is at less than 60% of its original height.

2. A method as claimed in claim 1, wherein each sample is alternately loaded and unloaded, each successive loading being performed by an equal force for a period whose length is determined by the attainment of a predetermined lower sample height; the first unloading period is equal to the first loading period and each successive unloading period is of a length which is determined by the attainment, in relaxation of the sample, of that height attained by the sample after the first unloading, the periods of loading and unloading for respective deformations being measured.

3. A method as claimed in claim 1, wherein the force applied to the sample is increased step-wise in each case until the material breaks down.

* * * * *

UNITED STATES PATENT AND TRADEMARK OFFICE
CERTIFICATE OF CORRECTION

PATENT NO. : 4,238,952
DATED : December 16, 1980
INVENTOR(S) : Rudiger Koopmann et al It is certified that error appears in the above–identified patent and that said Letters Patent are hereby corrected as shown below:

Col. 6, line 4, "in" should be --on--.

Signed and Sealed this

Thirty-first Day of March 1981

[SEAL]

Attest:

RENE D. TEGTMEYER

Attesting Officer　　　Acting Commissioner of Patents and Trademarks